US012780926B2

(12) United States Patent
Yea et al.

(10) Patent No.: US 12,780,926 B2
(45) Date of Patent: Nov. 3, 2026

(54) GFRAL-ANTAGONISTIC ANTIBODY HAVING IMPROVED AFFINITY, AND USE THEREOF

(71) Applicant: DAEGU GYEONGBUK INSTITUTE OF SCIENCE AND TECHNOLOGY, Daegu (KR)

(72) Inventors: Kyung Moo Yea, Daegu (KR); Beom Yong Lee, Daegu (KR); Jong Won Jeong, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 436 days.

(21) Appl. No.: 18/604,851

(22) Filed: Mar. 14, 2024

(65) Prior Publication Data

US 2024/0254242 A1 Aug. 1, 2024

Related U.S. Application Data

(63) Continuation of application No. PCT/KR2022/013279, filed on Sep. 5, 2022.

(30) Foreign Application Priority Data

Sep. 24, 2021 (KR) ........................ 10-2021-0126371
Aug. 29, 2022 (KR) ........................ 10-2022-0108398

(51) Int. Cl.
*C07K 16/28* (2006.01)
*A61K 39/00* (2006.01)
(Continued)

(52) U.S. Cl.
CPC .......... *C07K 16/2863* (2013.01); *A61K 39/00* (2013.01); *A61P 3/00* (2018.01);
(Continued)

(58) Field of Classification Search
CPC .......... C07K 16/2863; C07K 2317/565; C07K 2317/622; C07K 2317/33; C07K 2317/76;
(Continued)

(56) References Cited

U.S. PATENT DOCUMENTS 9,988,424 B2 * 6/2018 Haynes .................. A61K 39/12
10,358,497 B2 * 7/2019 Nioi .................. A61K 39/3955
(Continued)

FOREIGN PATENT DOCUMENTS

KR 20180130524 12/2018
KR 20210049840 5/2021
WO 2017/152105 9/2017

OTHER PUBLICATIONS

Chiu et al. (2019) Antibody structure and Function: Basis for Engineering Therapeutics Antibodies 8(55); 1-80 (Year: 2019).*
(Continued)

*Primary Examiner* — Joanne Hama
*Assistant Examiner* — Dasia A Aldarondo
(74) *Attorney, Agent, or Firm* — LEX IP MEISTER, PLLC

(57) ABSTRACT

The present invention relates to a GFRAL-antagonistic antibody having improved affinity and a use thereof, and more particularly, the present invention relates to an anti-GFRAL antibody having improved affinity, comprising a heavy chain CDR and a light chain CDR of specific sequences, or an antigen-binding fragment thereof. The anti-GFRAL antibody having improved affinity exhibits higher binding ability to a GFRAL protein than a conventional anti-GFRAL antibody, and thus is expected to be effectively used for improving or treating cancer-related anorexia or cachexia syndrome and side effects of chemotherapy anticancer drugs.

6 Claims, 10 Drawing Sheets

Specification includes a Sequence Listing.

(51) Int. Cl.
*A61P 1/14* (2006.01)
*A61P 3/00* (2006.01)

(52) U.S. Cl.
CPC .. *A61K 2039/505* (2013.01); *C07K 2317/565* (2013.01); *C07K 2317/622* (2013.01)

(58) Field of Classification Search
CPC ................ C07K 2317/92; A61K 39/00; A61K 2039/505; A61P 3/00; A61P 1/14
See application file for complete search history.

(56) References Cited

U.S. PATENT DOCUMENTS

| | | | | |
|---|---|---|---|---|
| 12,076,413 | B2 * | 9/2024 | Ganesan | A61K 47/6897 |
| 12,398,211 | B2 * | 8/2025 | Yea | C07K 16/28 |
| 2009/0202562 | A1 | 8/2009 | Worley et al. | |
| 2024/0084332 | A1 * | 3/2024 | Zhang | C12N 15/11 |

OTHER PUBLICATIONS

Teixeira and Erasmus et al. (2021) Drug-like antibodies with high affinity, diversity and developability directly from next generation antibody libraries mAbs 13(1) (Year: 2021).*
Rowena Suriben et al., "Antibody-mediated inhibition of GDF15-GFRAL activity reverses cancer cachexia in mice", Nature Medicine, vol. 26, pp. 1264-1270, Jul. 13, 2020.

* cited by examiner

[FIG. 1]
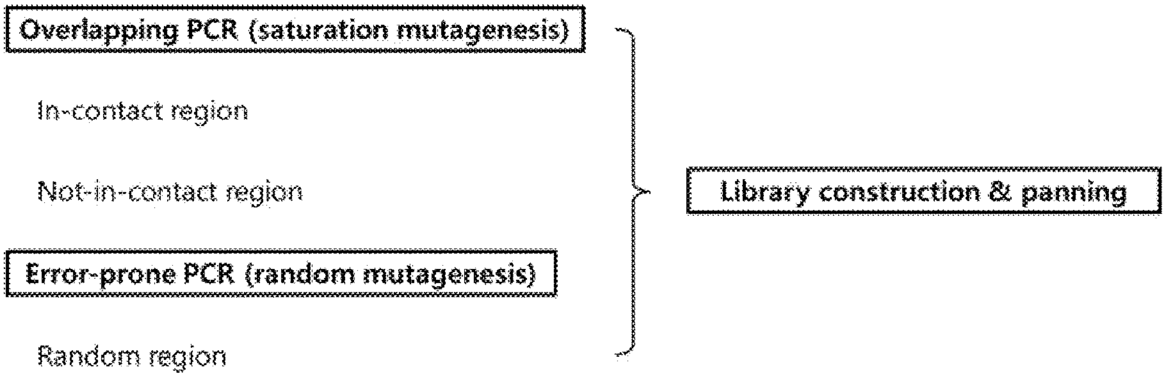
[FIG. 2]
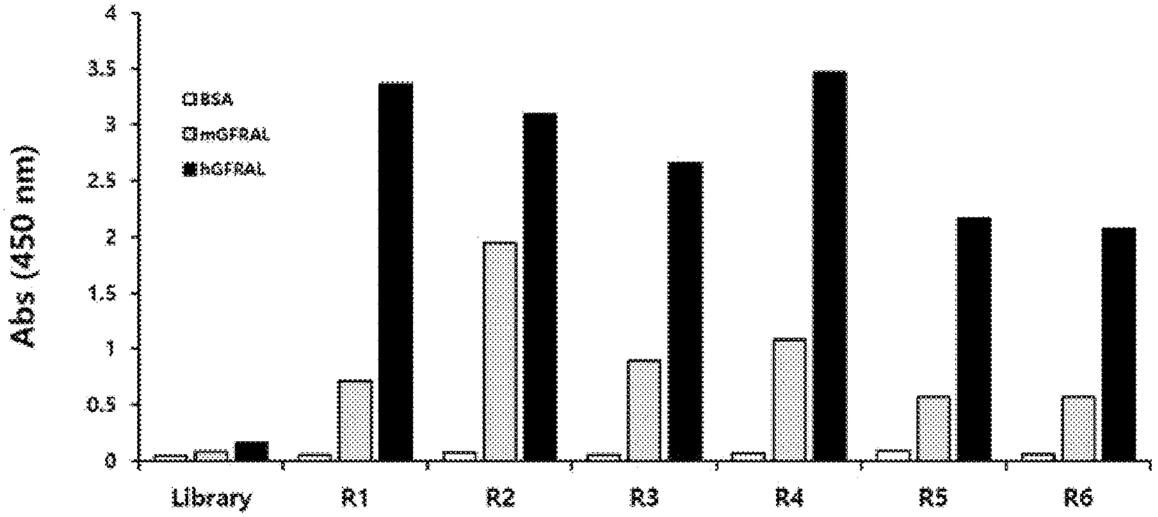

[FIG. 3]
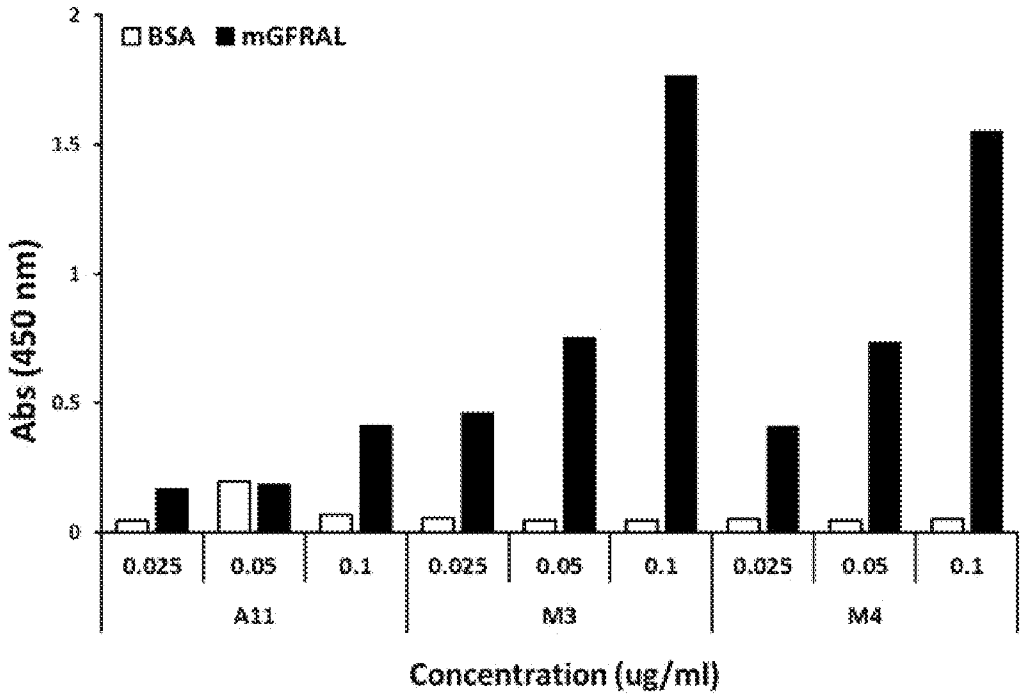
[FIG. 4]
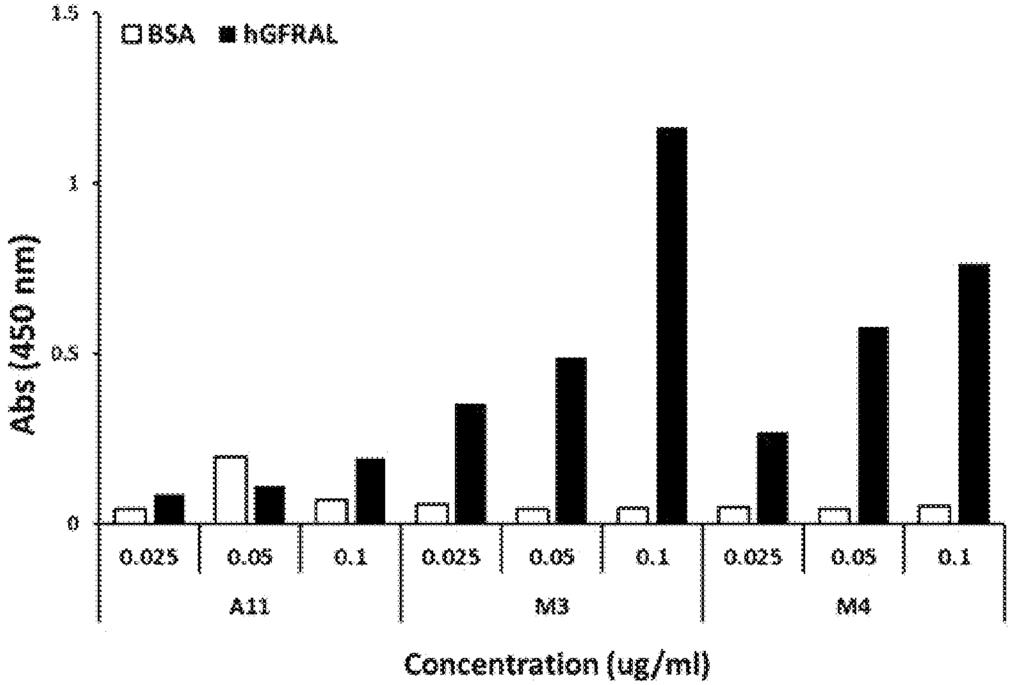

[FIG. 5]

| | VH CDR1 | VH CDR2 | VH CDR3 |
|---|---|---|---|
| A11 | GFTFSSYG (SEQ ID NO: 1) | ISYDGSNK (SEQ ID NO: 7) | CAKVTSGGDFWSGNYYYYMDV (SEQ ID NO: 11) |
| M3 | GFTFSSYG (SEQ ID NO: 1) | ISFDGSNK (SEQ ID NO: 2) | CAKVTSGGDFLSGNYYYYMDV (SEQ ID NO: 3) |
| M4 | GFTFSSYG (SEQ ID NO: 1) | ISYDGSNK (SEQ ID NO: 7) | CAKVTSGGDFWSGDYYWYMDV (SEQ ID NO: 8) |

| | VL CDR1 | VL CDR2 | VL CDR3 |
|---|---|---|---|
| A11 | SLRDYY (SEQ ID NO: 4) | GKN (SEQ ID NO: 5) | NSRGSSGNQWV (SEQ ID NO: 6) |
| M3 | SLRDYY (SEQ ID NO: 4) | GKN (SEQ ID NO: 5) | NSRGSSGNQWV (SEQ ID NO: 6) |
| M4 | SLRDNK (SEQ ID NO: 9) | GLN (SEQ ID NO: 10) | NSRGSSGNQWV (SEQ ID NO: 6) |

[FIG. 6]
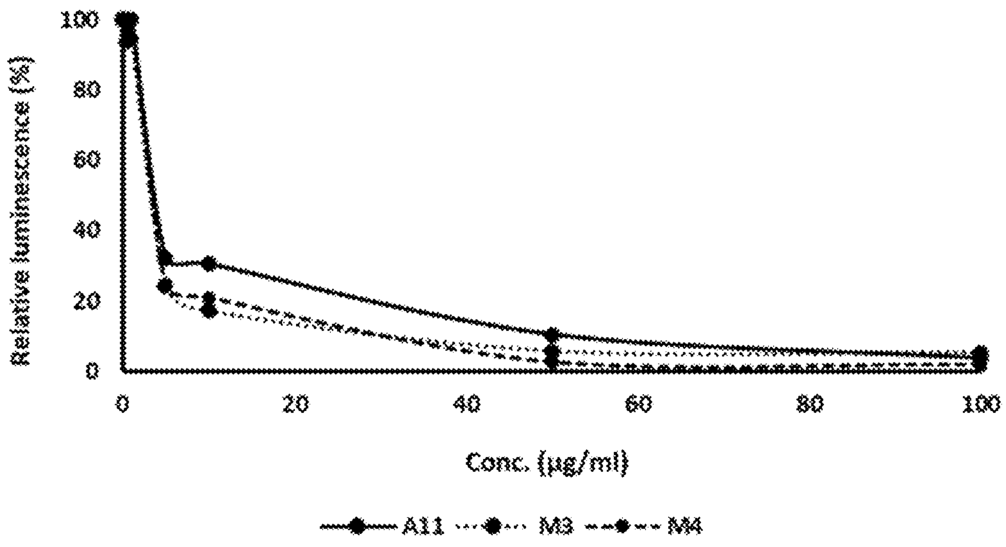

[FIG. 7]
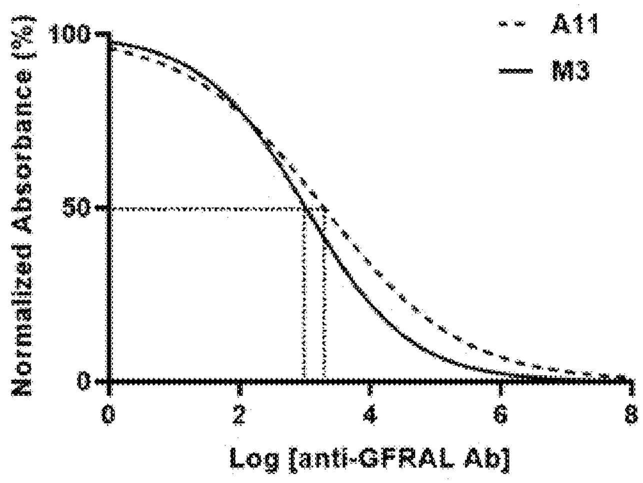
| | A11 | M3 |
|---|---|---|
| IC50 (μg/ml) | 1.959 | 1.034 |
[FIG. 8]
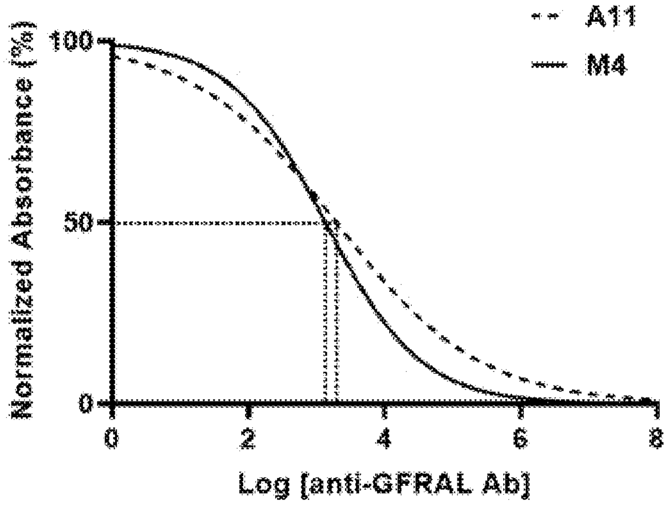
| | A11 | M4 |
|---|---|---|
| IC50 (μg/ml) | 1.959 | 1.354 |

[FIG. 9]
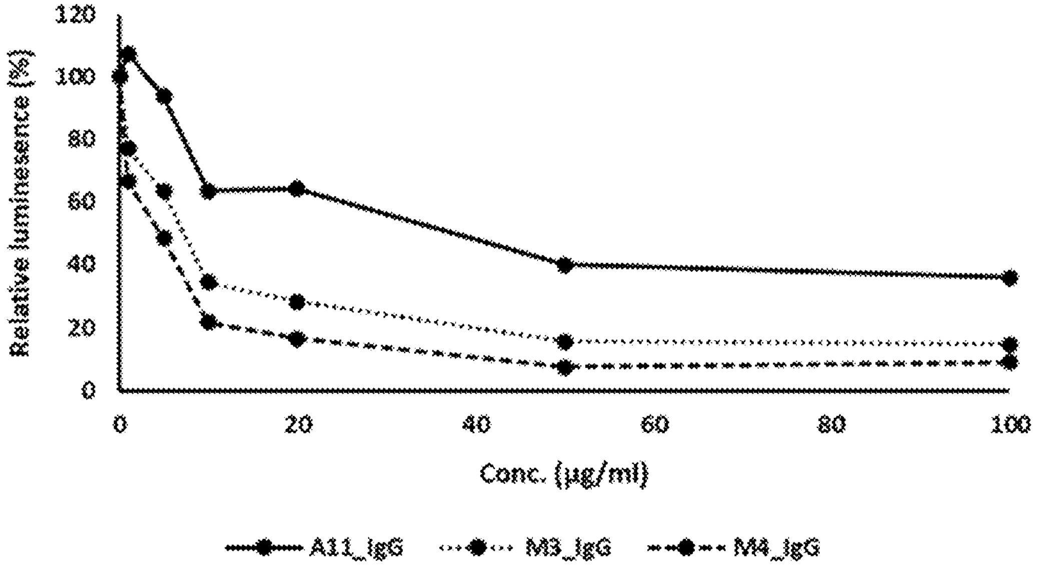
[FIG. 10]
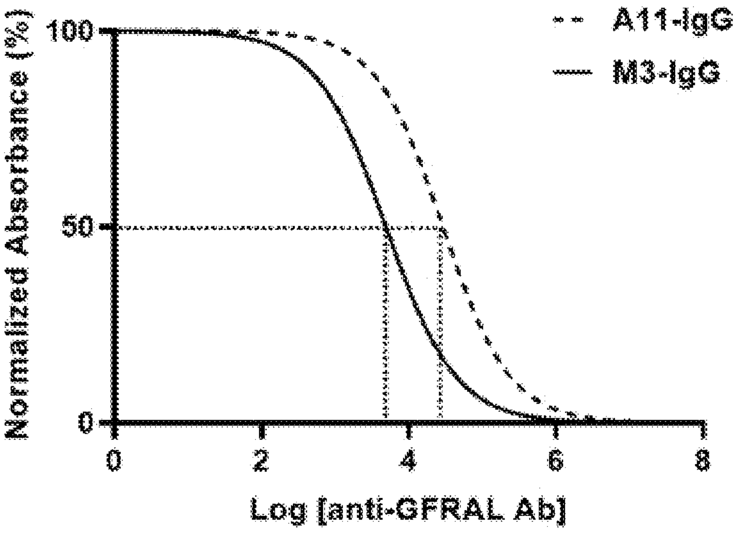
| | A11-IgG | M3-IgG |
|---|---|---|
| IC50 (μg/ml) | 29.08 | 4.889 |

[FIG. 11]
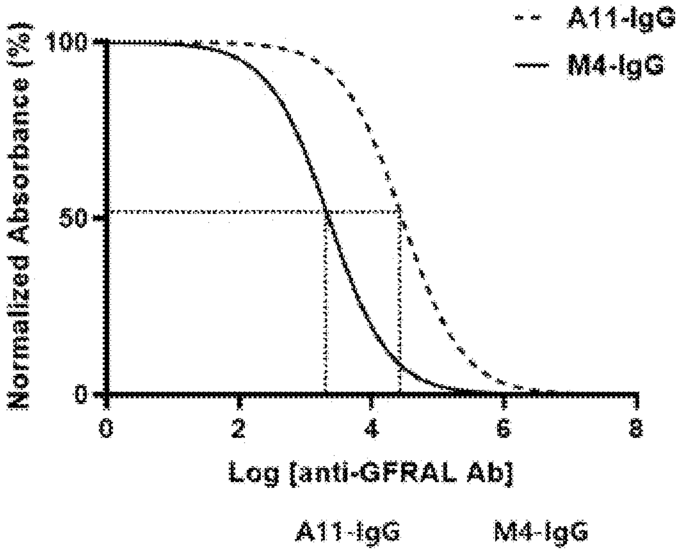
| | A11-IgG | M4-IgG |
|---|---|---|
| IC50 (μg/ml) | 29.08 | 2.259 |
[FIG. 12]
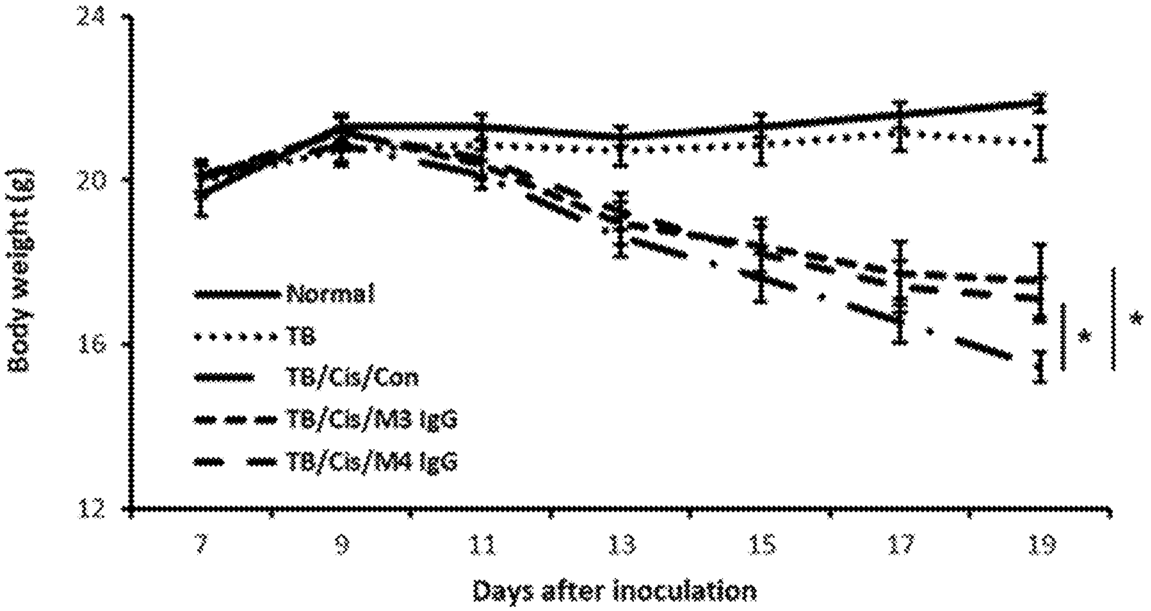

[FIG. 13]
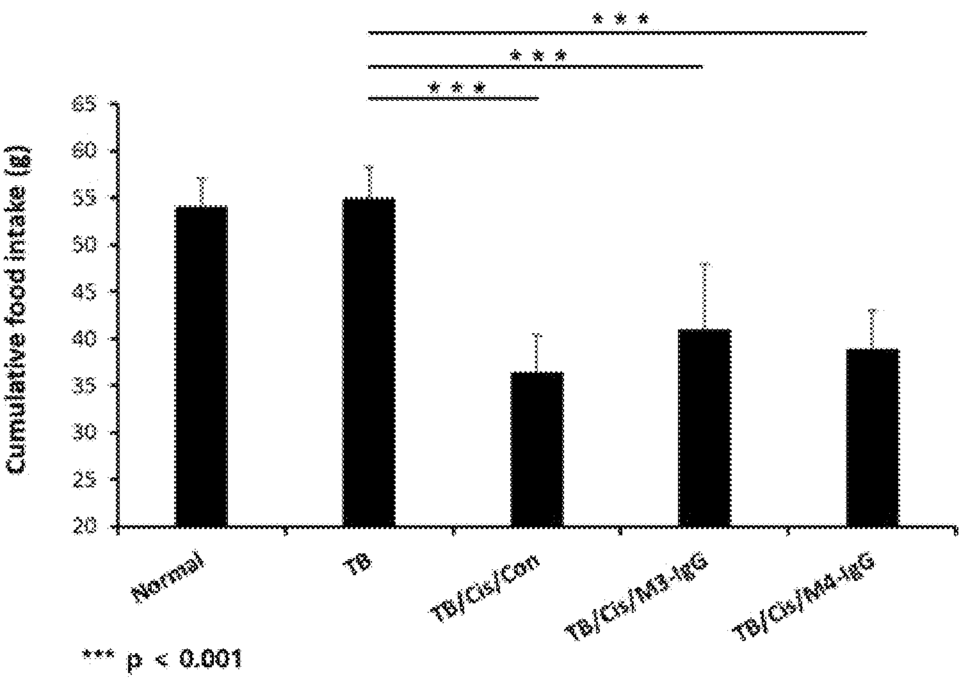
[FIG. 14]
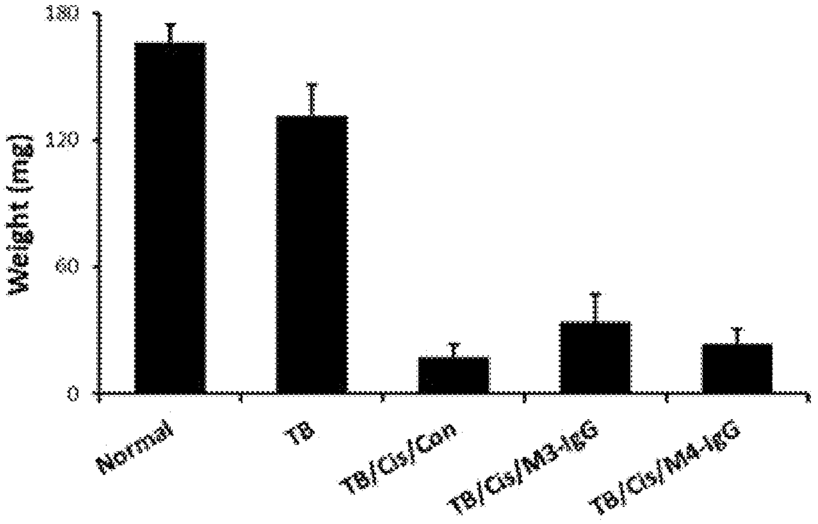

[FIG. 15]
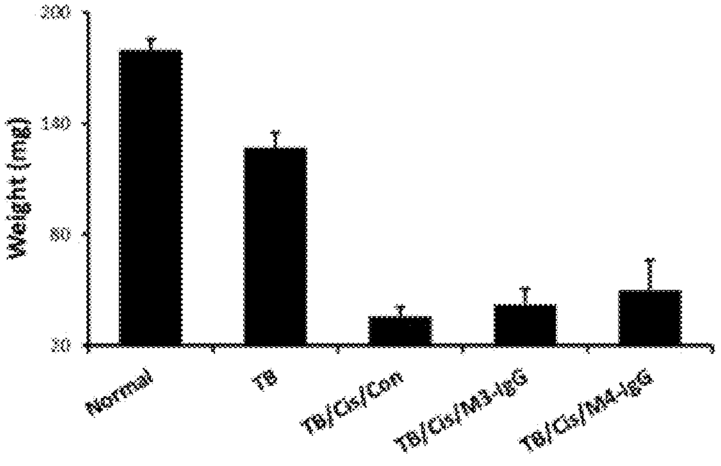
[FIG. 16]
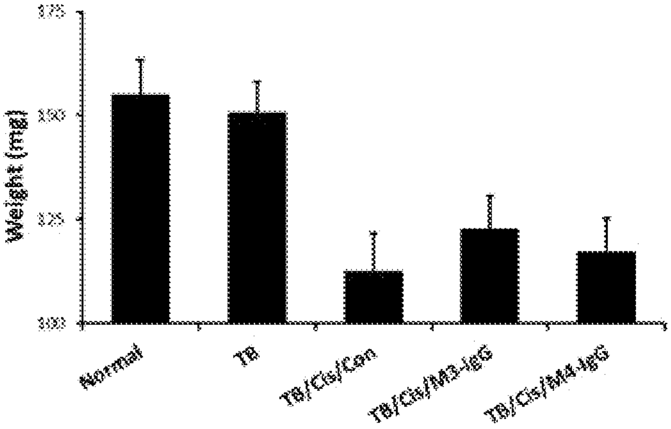

[FIG. 17]
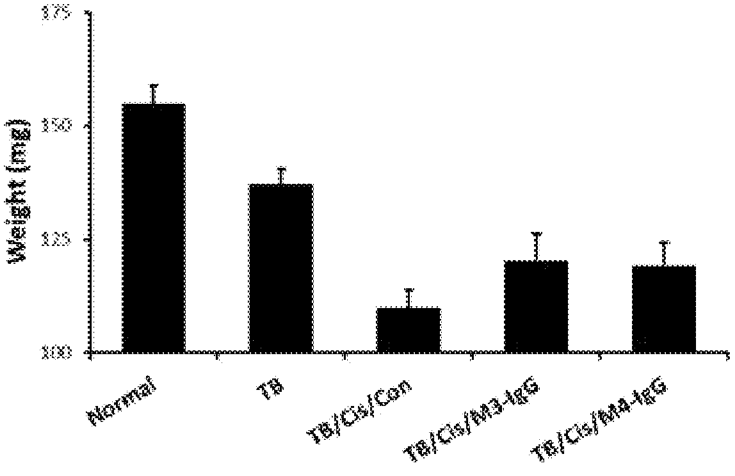
[FIG. 18]
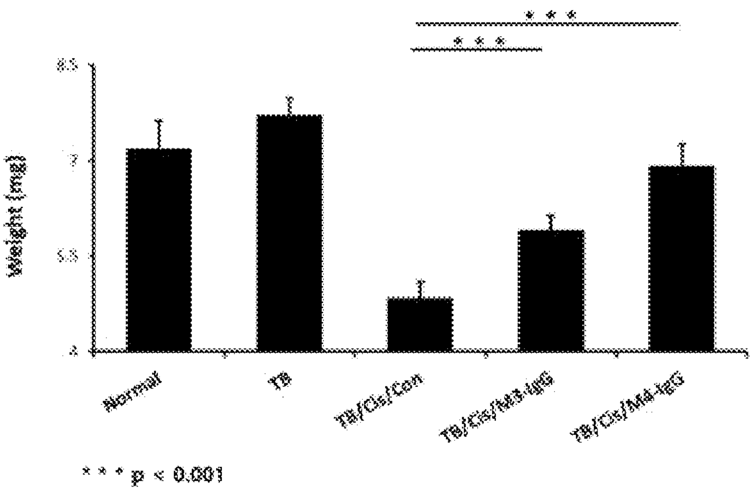

GFRAL-ANTAGONISTIC ANTIBODY HAVING IMPROVED AFFINITY, AND USE THEREOF

CROSS REFERENCE TO RELATED APPLICATIONS

This application is a Continuation of PCT International Patent Application No. PCT/KR2022/013279 filed on Sep. 5, 2022, which claims priority to Korean Patent Application Nos. 10-2021-0126371 filed on Sep. 24, 2021 and 10-2022-0108398 filed on Aug. 29, 2022 which are all hereby incorporated by reference in their entirety.

REFERENCE TO AN ELECTRONIC SEQUENCE LISTING

The contents of the electronic sequence listing (TPB20240055US_SEQ_revised.xml; Size: 9,340 bytes; and Date of Creation: Jul. 22, 2026) is herein incorporated by reference in its entirety. The contents of the electronic sequence listing in no way introduces new matter into the specification.

BACKGROUND OF THE INVENTION

The present disclosure relates to a GFRAL-antagonistic antibody with improved affinity and a use thereof.

Since the first monoclonal antibody was made in 1975, antibody therapy was launched for the first time in 1994 using characteristics of antibodies having strong binding affinity against antigens, and therapeutic antibodies have recorded the fastest growth among pharmaceuticals. As of 2007, the global market for therapeutic antibodies was valued at $27 billion, with a steady growth of $44.7 billion in 2011 and $57.7 billion in 2016. Based on this growth, the antibody drugs accounted for 10% of global drug sales in 2014, while antibody drugs take six of the top 10 drugs in sales in 2016. Compared to existing therapeutics based on chemical synthetics, antibody drugs have been proven to have relatively few side effects and outstanding therapeutic efficacy owing to high binding specificity and stability in vivo, and the field of antibody drug development is in the spotlight as a next-generation key field for new drug R&D. Alongside this, antibody drugs are expected to become the next-generation therapeutics due to the rapid development in expression, production, purification, and engineering technology for polymer proteins that are essential for development processes of antibody drugs as well as a high success rate in clinical trials.

Cancer-related anorexia-cachexia syndrome (CACS) refers to a state of excessive catabolism characterized by persistent anorexia and weight loss, which leads to an increase in muscle and fat breakdown, nutritional metabolic imbalance, and an increase in basal metabolic rate, thereby resulting in a decrease in overall physical functions. Such CACS is one of the important causes of death in cancer patients and the most important independent prognostic factor that enables prediction of negative treatment outcomes. Furthermore, it is accompanied by restriction of nutritional intake due to treatment such as chemotherapy, radiotherapy, or surgery to bring about a low response rate to treatment and difficulty in conducting efficient treatment, which is the main cause that degrades survival rate and quality of life of patients. Nonetheless, CACS is underestimated, and though there is still an unmet medical need, it is difficult, at this point, to expect effective treatment with general appetite stimulants and muscle synthesis stimulants.

Growth differentiation factor 15 (GDF15) is a cytokine that is involved in immune response and metabolism and has various functions in the body. Under normal circumstances, GDF15 is expressed in low concentrations in most tissues and increases significantly during damage in tissues such as the liver, kidneys, heart, and lungs. In 2007, it was revealed that GDF15 is a substance that induces cachexia through anorexia in the body of prostate cancer patients and that the concentration of GDF15 in the blood of prostate cancer patients increases 10 to 100 times that of normal people, suggesting a clear correlation between weight loss and GDF15 concentration by anorexia in cancer patients. In 2016, GDF15 was found to be a major cytokine that induces cachexia in various carcinomas, and GDF15 antibody showed improvement effects on cachexia by increasing body weight and mitigating loss of muscle and adipose tissues in mouse models with various cancer cachexia.

In 2015, it was found that expression of GDF15 increases as a side effect upon treatment of chemotherapy such as cisplatin, while resistance to chemotherapy increases by symptoms of anorexia and cachexia. In 2017, it was discovered that GDF15 suppresses appetite via the receptor GFRAL, and the signaling process of GDF15 after treatment of GDF15 alone or cisplatin is GFRAL-dependent. GFRAL, along with its co-receptor RET, transmits signals intracellularly and is expressed specifically in the hindbrain, area postrema (AP), and nucleus tractus solitarius (NTS) regions, which are outside the blood-brain barrier where antibody drugs are accessible.

Therefore, through administration of platinum anticancer drugs such as cisplatin, the anti-GFRAL antibodies may contribute to an increase in the well-being and life extension of cancer patients by improving anorexia in cancer patients undergoing CACS and reducing resistance to chemotherapy through weight gain and increased skeletal muscle metabolism.

DISCLOSURE OF THE INVENTION

SUMMARY OF THE INVENTION

An object of the present disclosure is to provide an anti-GFRAL antibody with improved affinity or an antigen-binding fragment thereof.

Another object of the present disclosure is to provide a nucleic acid molecule encoding the anti-GFRAL antibody with improved affinity or an antigen-binding fragment thereof, a recombinant expression vector including the nucleic acid molecule, and a cell transformed with the recombinant expression vector.

Another object of the present disclosure is to provide a composition for preventing, ameliorating, or treating cancer-related anorexia-cachexia syndrome (CACS), including the anti-GFRAL antibody with improved affinity or an antigen-binding fragment thereof as an active ingredient.

Another object of the present disclosure is to provide a composition for preventing, ameliorating, or treating anorexia or cachexia caused by anticancer drugs, including the anti-GFRAL antibody with improved affinity or an antigen-binding fragment thereof as an active ingredient.

In order to achieve the above objects, the present disclosure provides an anti-GFRAL antibody with improved affinity or an antigen-binding fragment thereof, including a heavy chain variable region which includes a heavy chain CDR1 having an amino acid sequence represented by SEQ ID NO: 1, a heavy chain CDR2 having an amino acid sequence represented by SEQ ID NO: 2, and a heavy chain CDR3 having an amino acid sequence represented by SEQ ID NO: 3; and a light chain variable region which includes a light chain CDR1 having an amino acid sequence represented by SEQ ID NO: 4, a light chain CDR2 having an amino acid sequence represented by SEQ ID NO: 5, and a light chain CDR3 having an amino acid sequence represented by SEQ ID NO: 6.

In addition, the present disclosure provides an anti-GFRAL antibody with improved affinity or an antigen-binding fragment thereof, including a heavy chain variable region which includes a heavy chain CDR1 having an amino acid sequence represented by SEQ ID NO: 1, a heavy chain CDR2 having an amino acid sequence represented by SEQ ID NO: 7, and a heavy chain CDR3 having an amino acid sequence represented by SEQ ID NO: 8; and a light chain variable region which includes a light chain CDR1 having an amino acid sequence represented by SEQ ID NO: 9, a light chain CDR2 having an amino acid sequence represented by SEQ ID NO: 10, and a light chain CDR3 having an amino acid sequence represented by SEQ ID NO: 6.

In addition, the present disclosure provides a nucleic acid molecule encoding the anti-GFRAL antibody with improved affinity or an antigen-binding fragment thereof.

In addition, the present disclosure provides a recombinant expression vector including the nucleic acid molecule.

In addition, the present disclosure provides a cell transformed with the recombinant expression vector.

In addition, the present disclosure provides a pharmaceutical composition for preventing or treating cancer-related anorexia-cachexia syndrome (CACS), including the anti-GFRAL antibody with improved affinity or an antigen-binding fragment thereof as an active ingredient.

In addition, the present disclosure provides a health functional food composition for preventing or ameliorating cancer-related anorexia-cachexia syndrome (CACS), including the anti-GFRAL antibody with improved affinity or an antigen-binding fragment thereof as an active ingredient.

In addition, the present disclosure provides a pharmaceutical composition for preventing or treating anorexia or cachexia caused by an anticancer drug, including the anti-GFRAL antibody with improved affinity or an antigen-binding fragment thereof as an active ingredient.

In addition, the present disclosure provides a health functional food composition for preventing or ameliorating anorexia or cachexia caused by an anticancer drug, including the anti-GFRAL antibody with improved affinity or an antigen-binding fragment thereof as an active ingredient.

The present disclosure relates to a GFRAL-antagonistic antibody with improved affinity and a use thereof, and more specifically, the present disclosure relates to an anti-GFRAL antibody which includes a heavy chain CDR and a light chain CDR of a specific sequence and has improved affinity, or an antigen-binding fragment thereof. The anti-GFRAL antibody with improved affinity shows higher binding ability to GFRAL proteins than conventional anti-GFRAL antibodies, and thus it is expected to be useful in alleviating or treating cancer-related anorexia-cachexia syndrome and side effects of chemotherapy anticancer drugs.

BRIEF DESCRIPTION OF DRAWINGS

FIG. 1 shows three types of transformation methods using conventional anti-GFRAL antibodies to enhance a binding ability to GFRAL. A total of 3 types of mutations were made, wherein a first mutation had modification in an amino acid sequence of a site that binds with GFRAL, a second mutation had modification in an amino acid sequence of a site that does not bind with GFRAL, and a third mutation had random modification in a scFv-Fc site.

FIG. 2 shows a result of determining a binding ability of a bacteriophage library to GFRAL via polyphage enzyme-linked immunosorbent assay. The result was derived by performing a total of 6 pannings, with separation involved by binding ability with mouse and human GFRAL.

FIG. 3 shows a result of identifying a binding ability of two kinds of monoclones to GFRAL after performing monophage enzyme-linked immunosorbent assay on mouse GFRAL. After performing the panning 6 times, as a result of identifying the binding ability to GFRAL by separating with monoclonal antibodies among finally selected antibodies, it was determined that the binding ability of two kinds of antibodies out of about 100 kinds to mouse GFRAL was higher than that of existing A11.

FIG. 4 shows a result of identifying a binding ability of two kinds of monoclones to GFRAL after conducting monophage enzyme-linked immunosorbent assay on human GFRAL. After performing the panning 6 times, as a result of identifying the binding ability to GFRAL by separating with monoclonal antibodies among finally selected antibodies, it was determined that the binding ability of two kinds of antibodies out of about 100 kinds to human GFRAL was higher than that of existing A11.

FIG. 5 shows a result of identifying amino acid sequences of each CDR site of two kines of monoclones. After identifying the amino acid sequences of the two kinds of monoclones, it was found that there was a mutation (shown in red) occurred in the sequence.

FIG. 6 shows a result of reduction in luciferase expression by monoclones scFv-Fc A11, M3, and M4 in GFRAL/RET/luciferase overexpressing cells via a reporter assay. The reporter assay was conducted to determine whether the two kinds of selected monoclonal antibodies, M3 and M4, inhibit a signaling mechanism of GFRAL, showing that M3 and M4 inhibit the signaling mechanism of GFRAL more than the existing A11.

FIG. 7 shows a numerical result of comparison between A11 and M3 from the results of FIG. 6 via densitometry. Based on the above results, as a result of quantifying a degree of GFRAL inhibition, it was found that a concentration of antibodies required for a 50% inhibitory effect was 1.959 ug/ml for conventional A11 and 1.034 ug/ml for M3, indicating that a signal of GFRAL is inhibited with a smaller amount.

FIG. 8 shows a numerical result of comparison between A11 and M4 from the results of FIG. 6 via densitometry. Based on the above results, as a result of quantifying a degree of GFRAL inhibition, it was found that a concentration of antibodies required for a 50% inhibitory effect was 1.959 ug/ml for conventional A11 and 1.354 ug/ml for M4, indicating that a signal of GFRAL is inhibited with a smaller amount.

FIG. 9 shows a result of identifying, via reporter assay, reduction in luciferase expression by A11, M3, and M4 made from human IgG antibodies in GFRAL/RET/luciferase overexpressing cells. The selected two kinds of monoclonal antibodies, M3 and M4, were made from human IgG antibodies, and the same experiment as the FIG. 6 was carried out to see if the same results are obtained. It was found that M3-IgG and M4-IgG, made from human IgG antibodies, inhibit the signaling mechanism of GFRAL 5 times more than conventional A11.

FIG. 10 shows a numerical result of comparison between A11 and M3 from the results of FIG. 9 via densitometry. Based on the above results, as a result of quantifying a degree of GFRAL inhibition, it was found that a concentration of antibodies required for a 50% inhibitory effect was 29.08 ug/ml for conventional A11-IgG and 4.889 ug/ml for M3-IgG, indicating that a signal of GFRAL is inhibited with about 5 times smaller amount.

FIG. 11 shows a numerical result of comparison between A11 and M4 from the results of FIG. 9 via densitometry. Based on the above results, as a result of quantifying a degree of GFRAL inhibition, it was found that a concentration of antibodies required for a 50% inhibitory effect was 29.08 ug/ml for conventional A11-IgG and 2.259 ug/ml for M4-IgG, indicating that a signal of GFRAL is inhibited about 10 times more than M3-IgG with 2 times smaller amount.

FIG. 12 shows a result of identifying mitigation of a weight loss effect of cisplatin by monoclones M3 and M4 in an allograft mouse tumor model. 10 mpk of cisplatin was inoculated to tumor model mice prepared by inoculating melanoma cancer cells in order to induce cancer cachexia. As a result of observing weight loss, which is a typical symptom of cancer cachexia, it was found that a weight decreased by 30% 10 days after cisplatin injection. To identify a cancer cachexia mitigation effect by anti-GFRAL antibodies, compared to a group treated with cisplatin alone out of those treated with cisplatin and antibodies, there was a 13% increase effect shown in a case of monoclonal antibody M3-IgG and a 10% increase effect in M4-IgG.

FIG. 13 shows a result of identifying mitigation on an appetite-reduction effect of cisplatin by monoclones M3 and M4 in an allograft mouse tumor model. As a result of identifying reduction in the appetite loss, which is one of the typical symptoms of cancer cachexia, it was found that an amount of food intake was reduced in a cisplatin-injected group. To identify a cancer cachexia mitigation effect by anti-GFRAL antibodies, compared to a group treated with cisplatin alone out of those treated with cisplatin and antibodies, there was a 12% increase effect shown in a case of monoclonal antibody M3-IgG and a 7% increase effect in M4-IgG.

FIG. 14 shows a result of identifying mitigation on an eWAT fat mass reduction effect of cisplatin by monoclones M3 and M4 in an allograft mouse tumor model. As a result of identifying reduction in eWAT fat mass, a decrease in eWAT fat mass was observed in a cisplatin-injected group. To identify a cancer cachexia mitigation effect by anti-GFRAL antibodies, compared to a group treated with cisplatin alone out of those treated with cisplatin and antibodies, there was a 90% increase effect shown in a case of monoclonal antibody M3-IgG and a 30% increase effect in M4-IgG.

FIG. 15 shows a result of identifying mitigation on an iWAT fat mass reduction effect of cisplatin by monoclones M3 and M4 in an allograft mouse tumor model. As a result of identifying reduction in iWAT fat mass, a decrease in iWAT fat mass was observed in a cisplatin-injected group. To identify a cancer cachexia mitigation effect by anti-GFRAL antibodies, compared to a group treated with cisplatin alone out of those treated with cisplatin and antibodies, there was a 17% increase effect shown in a case of monoclonal antibody M3-IgG and a 40% increase effect in M4-IgG.

FIG. 16 shows a result of identifying mitigation on a quadriceps muscle mass reduction effect of cisplatin by monoclones M3 and M4 in an allograft mouse tumor model.

As a result of identifying reduction in quadriceps muscle mass, a decrease in quadriceps muscle mass was observed in a cisplatin-injected group. To identify a cancer cachexia mitigation effect by anti-GFRAL antibodies, compared to a group treated with cisplatin alone out of those treated with cisplatin and antibodies, there was a 9% increase effect shown in a case of monoclonal antibody M3-IgG and a 4% increase effect in M4-IgG.

FIG. 17 shows a result of identifying mitigation on a gastrocnemius muscle mass reduction effect of cisplatin by monoclones M3 and M4 in an allograft mouse tumor model. As a result of identifying reduction in gastrocnemius muscle mass, a decrease in gastrocnemius muscle mass was observed in a cisplatin-injected group. To identify a cancer cachexia mitigation effect by anti-GFRAL antibodies, compared to a group treated with cisplatin alone out of those treated with cisplatin and antibodies, there was a 10% increase effect shown in a case of monoclonal antibody M3-IgG and a 9% increase effect in M4-IgG.

FIG. 18 shows a result of identifying mitigation on a soleus muscle mass reduction effect of cisplatin by monoclones M3 and M4 in an allograft mouse tumor model. As a result of identifying reduction in a soleus muscle mass, a decrease in the soleus muscle mass was observed in a cisplatin-injected group. To identify a cancer cachexia mitigation effect by anti-GFRAL antibodies, compared to a group treated with cisplatin alone out of those treated with cisplatin and antibodies, there was a 20% increase effect shown in a case of monoclonal antibody M3-IgG and a 40% increase effect in M4-IgG.

DETAILED DESCRIPTION OF THE INVENTION

The present disclosure provides an anti-GFRAL antibody with improved affinity or an antigen-binding fragment thereof, including a heavy chain variable region which includes a heavy chain CDR1 having an amino acid sequence represented by SEQ ID NO: 1, a heavy chain CDR2 having an amino acid sequence represented by SEQ ID NO: 2, and a heavy chain CDR3 having an amino acid sequence represented by SEQ ID NO: 3; and a light chain variable region which includes a light chain CDR1 having an amino acid sequence represented by SEQ ID NO: 4, a light chain CDR2 having an amino acid sequence represented by SEQ ID NO: 5, and a light chain CDR3 having an amino acid sequence represented by SEQ ID NO: 6.

Further, the present disclosure provides an anti-GFRAL antibody with improved affinity or an antigen-binding fragment thereof, including a heavy chain variable region which includes a heavy chain CDR1 having an amino acid sequence represented by SEQ ID NO: 1, a heavy chain CDR2 having an amino acid sequence represented by SEQ ID NO: 7, and a heavy chain CDR3 having an amino acid sequence represented by SEQ ID NO: 8; and a light chain variable region which includes a light chain CDR1 having an amino acid sequence represented by SEQ ID NO: 9, a light chain CDR2 having an amino acid sequence represented by SEQ ID NO: 10, and a light chain CDR3 having an amino acid sequence represented by SEQ ID NO: 6.

In addition, the CDRs having amino acids represented by SEQ ID NO: 1 to SEQ ID NO: 10 are listed in Table 1 below.

TABLE 1

| | VH | | | VL | | |
|---|---|---|---|---|---|---|
| | CDR1 | CDR2 | CDR3 | CDR1 | CDR2 | CDR3 |
| A11 | GFTFSSYG | ISYDGSNK | CAKVTSGGDF WSGNYYYYM DV | SLRDYY | GKN | NSRGSSG NQWV |
| M3 | GFTFSSYG (SEQ ID NO: 1) | ISFDGSNK (SEQ ID NO: 2) | CAKVTSGGDF LSGNYYYYM DV (SEQ ID NO: 3) | SLRDYY (SEQ ID NO: 4) | GKN (SEQ ID NO: 5) | NSRGSSG NQWV (SEQ ID NO: 6) |
| M4 | GFTFSSYG (SEQ ID NO: 1) | ISYDGSNK (SEQ ID NO: 7) | CAKVTSGGDF WSGDYYWY MDV (SEQ ID NO: 8) | SLRDNK (SEQ ID NO: 9) | GLN (SEQ ID NO: 10) | NSRGSSG NQWV (SEQ ID NO: 6) |

The term "antibody" as used herein refers to a protein molecule which includes an immunoglobulin molecule that is immunologically reactive with a specific antigen and serves as a receptor specifically recognizing an antigen, and it may all include, for example, a monoclonal antibody, polyclonal antibody, full-length antibody, and antibody fragment. In addition, the term "antibody" may include bivalent or bispecific molecules (such as bispecific antibodies), diabodies, triabodies, or tetrabodies.

As used herein, the term "monoclonal antibody" refers to an antibody molecule of a single molecular composition obtained from a substantially identical antibody population, and such a monoclonal antibody exhibits single binding properties and affinity for a particular epitope, whereas a polyclonal antibody may bind to multiple epitopes. As used herein, the term "full-length antibody" is in a structure having two full-length light chains and two full-length heavy chains, each of which is connected to a heavy chain via a disulfide bond. The heavy chain constant region has gamma (γ), mu (μ), alpha (α), delta (δ), and epsilon (ε) types, and has gamma1 (γ1), gamma2 (γ2), gamma3 (γ3), gamma4 (γ4), alpha1 (α1), and alpha2 (α2) as subclasses. The constant regions of the light chain have kappa (κ) and lambda (λ) types. IgG is a subtype, which includes IgG1, IgG2, IgG3, and IgG4.

As used herein, the term "heavy chain" may all include a full-length heavy chain and fragments thereof, including a variable region VH having an amino acid sequence with a variable domain sequence sufficient to give specificity to the antigen as well as three constant regions CH1, CH2, and CH3. In addition, as used herein, the term "light chain" may all include a full-length light chain and fragments thereof, including a variable region VL having an amino acid sequence with a variable domain sequence sufficient to give specificity to the antigen as well as constant region CL.

As used herein, the terms "fragment", "antibody fragment" and "antigen-binding fragment" are used interchangeably to refer to any fragment of the antibody of the present disclosure that possesses an antigen-binding function of the antibody. Exemplary antigen-binding fragments include, but are not limited to, Fab, Fab', F(ab')2, and Fv.

The antibody of the present disclosure or an antigen-binding fragment thereof may include, to the extent that it may exhibit an ability to specifically bind to GFRAL, a sequence of the antibody described herein, as well as the biological equivalents thereof. For example, additional modifications may be made to the amino acid sequence of the antibody in order to further improve the binding affinity and/or other biological properties of the antibody. These modifications include, for example, deletion, insertion and/or substitution of amino acid sequence residues of antibodies. These amino acid mutations are based on the relative similarity of amino acid side chain substituents, such as hydrophobicity, hydrophilicity, charge, and size. According to analysis on the size, shape, and type of amino acid side chain substituents, it may be noticed that arginine, lysine, and histidine are all positively charged residues; alanine, glycine, and serine have similar sizes; and phenylalanine, tryptophan, and tyrosine have similar shapes. Thus, based on this, arginine, lysine, and histidine; alanine, glycine, and serine; and phenylalanine, tryptophan, and tyrosine may be biologically functional equivalents.

In addition, the present disclosure provides a nucleic acid molecule encoding the anti-GFRAL antibody with improved affinity or an antigen-binding fragment thereof.

As used herein, the term "nucleic acid molecule" has a comprehensive meaning to include DNA (gDNA and cDNA) and RNA molecules, and nucleotides, which are the basic building blocks of nucleic acid molecules, include not only natural nucleotides, but also analogues with sugar or base sites modified. The sequence of nucleic acid molecules encoding the heavy and light chain variable regions of the present disclosure may be modified, and the modification includes addition, deletion, or non-conservative substitution or conservative substitution of nucleotides.

In addition, the present disclosure provides a recombinant expression vector including the nucleic acid molecule.

As used herein, the term "vector" refers to a self-replicating DNA molecule used to carry a clonal gene (or another piece of clonal DNA).

As used herein, the term "expression vector" refers to a recombinant DNA molecule including a desired coding sequence and an appropriate nucleic acid sequence essential to express the coding sequence operably linked in a particular host organism. The expression vector may preferably include one or more selective markers. The marker is a nucleic acid sequence with properties that may conventionally be selected by conventional chemical means, including any gene that may distinguish a transformed cell from non-transgenic cells. Examples include, but are not limited to, antibiotic resistant genes such as ampicillin, kanamycin, geneticin (G418), bleomycin, hygromycin, and chloramphenicol, and it may be appropriately selected by those skilled in the art.

In order to express the DNA sequence of the present disclosure, any of the very diverse expression regulatory sequences may be used in the vector. Examples of useful expression regulatory sequences may include, for example, early and late promoters of SV40 or adenovirus, promoters and enhancers of CMV, LTR, lac systems, trp systems, TAC or TRC systems, and T3 and T7 promoters of retroviruses, major operators and promoter domains of phage lambdas, regulatory regions of fd code proteins, promoters of 3-phosphoglycerate kinase or other glycolase, promoters of the phosphatase, e.g., Pho5, promoters of the yeast alpha-hybridization system and other sequences of composition and derivation known to regulate the expression of genes in prokaryotic or eukaryotic cells or their viruses, and several combinations thereof.

The vector expressing the antibody of the present disclosure may be either a vector system in which the light and heavy chains are expressed simultaneously in a single vector, or a system in which the light and heavy chains are expressed in separate vectors. In the latter case, both vectors are introduced into a host cell through co-transformation and targeted transformation. Co-transformation is a method of simultaneously introducing each vector DNA encoding light and heavy chains into the host cell and then screening cells that express both light and heavy chains. Targeted transformation is a method of screening cells that have been transformed with a vector including a light chain (or a heavy chain) and then transfecting screened cells expressing a light chain back into a vector including a heavy chain (or a light chain) to finally screen cells expressing both light and heavy chains.

In addition, the present disclosure provides a cell transformed with a recombinant expression vector.

Cells capable of stable and continuous cloning and expression of the vector of the present disclosure may be any host cell known in the art, including, for example, strains in the genus *Bacillus* such as *Escherichia coli, Bacillus subtilis*, and *Bacillus thuringiensis*, and prokaryotic host cells such as *Streptomyces, Pseudomonas* (e.g., *Pseudomonas putida*), *Proteus mirabilis*, or *Staphylococcus* (e.g., *Staphylococcus carnosus*), but are not limited to.

The culture of transgenic cells in a preparation method of the antibody or an antigen-binding fragment thereof may be carried out in accordance with a suitable medium and culture conditions known in the relevant technical field. A person skilled in the art may handle this culture process with easy adjustment depending on the selected strain. Cell culture is divided into suspension culture and adherent culture depending on the cell growth types, and batch, fed-batch, and continuous culture methods depending on the culture types. The medium used for culture must adequately meet requirements of the specific strain.

In addition, the present disclosure provides a pharmaceutical composition for preventing or treating cancer-related anorexia-cachexia syndrome (CACS), including the anti-GFRAL antibody with improved affinity or an antigen-binding fragment thereof as an active ingredient.

The pharmaceutical composition of the present disclosure may additionally include a pharmaceutically acceptable carrier, and the pharmaceutically acceptable carrier is commonly used in the preparation, including, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methyl hydroxybenzoate, propylhydroxybenzoate, talc, magnesium stearate, and mineral oil. The pharmaceutical composition of the present disclosure may further include lubricants, wetting agents, sweeteners, flavoring agents, emulsifiers, suspensions, and preservatives, in addition to the above components.

The pharmaceutical composition of the present disclosure may be administered orally or parenterally, and in the case of parenteral administration, it may be administered by intravenous infusion, subcutaneous infusion, intramuscular infusion, abdominal infusion, endothelial administration, topical administration, intranasal administration, intrapulmonary administration, and rectal administration. When administered orally, since the protein or peptide is digested, the composition for oral administration may be formulated to coat the active agent or to protect it from degradation in the stomach, and the composition of the present disclosure may be administered by any device by which the active substance may be transported to a target cell.

The appropriate dosage of the pharmaceutical composition of the present disclosure varies depending on factors such as formulation method, mode of administration, patient's age, weight, sex, condition, food, time of administration, route of administration, excretion rate, and response sensitivity, and usually a skilled physician may easily determine and prescribe an effective dosage for the desired treatment or prevention.

The pharmaceutical composition of the present disclosure may be prepared in a unit-volume form or prepared by introducing in a multi-volume container through formulation using pharmaceutically acceptable carriers and/or excipients according to a method that may be easily carried out by a person skilled in the art to which the present disclosure pertains. In this case, the formulation may be in the form of a solution, suspension, or emulsion in an oil or aqueous medium, or it may be in the form of an extract, acid, suppository, powder, granule, tablet, or capsule, and it may additionally include a dispersant or stabilizer.

In addition, the present disclosure provides a health functional food composition for preventing or ameliorating cancer-related anorexia-cachexia syndrome (CACS), including the anti-GFRAL antibody with improved affinity or an antigen-binding fragment thereof as an active ingredient.

The health functional food composition may be provided in the form of powder, granules, tablets, capsules, syrups, beverages, or pills, and the health food composition may be used in combination with other foods or food additives in addition to the composition according to the present disclosure, which is the active ingredient, and may be used appropriately in accordance with the conventional methods. The mixed amount of the active ingredient may be appropriately determined depending on purpose of its use, e.g. preventive, health or therapeutic treatment.

The effective dose of the antibody or the antigen-binding fragment thereof included in the health functional food composition may be used in accordance with the effective dose of the pharmaceutical composition, but in the case of long-term intake for the purpose of health and hygiene or for the purpose of health control, it may be below the above range, and it is certain that the active ingredient may be used in an amount beyond the above range since there is no problem in terms of safety.

There is no specific limitation on the types of health foods, such as meat, sausages, bread, chocolate, candy, snacks, confectionery, pizza, ramen, other noodles, chewing gum, dairy products including ice cream, various soups, beverages, tea, drinks, alcoholic beverages, and vitamin complexes.

In addition, the present disclosure provides a pharmaceutical composition for preventing or treating anorexia or cachexia caused by an anticancer drug, including the anti- GFRAL antibody with improved affinity or an antigen-binding fragment thereof as an active ingredient.

In addition, the present disclosure provides a health functional food composition for preventing or ameliorating anorexia or cachexia caused by an anticancer drug, including the anti-GFRAL antibody with improved affinity or an antigen-binding fragment thereof as an active ingredient.

More preferably, the anticancer drug may be, but is not limited to, any one or more selected from the group consisting of cisplatin, oxaliplatin, carboplatin, procarbazine, mechlorethamine, cyclophosphamide, ifosfamide, melphalan, chlorambucil, busulfan, nitrosourea, dactinomycin, daunorubicin, doxorubicin, bleomycin, plicamycin, mitomycin, etoposide, tamoxifen, taxol, transplatinum, 5-fluorouracil, vincristine, vinblastine, and methotrexate.

In addition, the anti-GFRAL antibody of the present disclosure or an antigen-binding fragment thereof may be used as an anticancer adjuvant. As used herein, an anticancer adjuvant refers to those capable of alleviating side effects induced upon administration of anticancer drugs. In other words, by administering the anticancer adjuvant of the present disclosure in combination with the anticancer drug, it is possible to prevent occurrence of various side effects induced by anticancer drugs. The adjuvant of the present disclosure may be administered simultaneously, separately, or sequentially with the anticancer drug. The order of administration of the anticancer adjuvant according to the present disclosure, that is, whether to administer the anticancer drug or the anticancer adjuvant at any point in time, simultaneously, separately, or sequentially, may be determined by a doctor or specialist. This order of administration may vary depending on many factors.

Hereinafter, the present disclosure will be described in more detail through example embodiments. These example embodiments are only for illustrating the present disclosure in more detail, and it will be apparent to those skilled in the art that the scope of the present disclosure is not limited by these example embodiments according to the gist of the present disclosure.

<Example 1> Cell Culture

HEK-293FT cells (human embryonic kidney) were cultured in DMEM medium (Hyclone) supplemented with 10% fetal bovine serum, 1% penicillin, and streptomycin, and Expi-293F cells (human embryonic kidney) were cultured in Expi-293 expression medium (Gibco).

<Example 2> Polyclonal Phage Enzyme-Linked Immunosorbent Assay

A 96-well half area plate (#3690, Corning) was coated by a reaction with recombinant human GFRAL or recombinant mouse GFRAL, or bovine serum albumin overnight at 4° C. and then washed once using PBS. Afterwards, blocking was performed for 1 hour at 37° C. with PBS including 5% skim milk. Thereafter, a reaction was followed with the phage library for each round for 2 hours at 37° C., washing was performed 5 times using PBS followed by a reaction with HRP-conjugated anti-phage antibody (#11973-MM05T-H, Sino Biological) for 1 hour at 37° C., and then washing was performed 5 times with PBS. Lastly, the color was developed at room temperature for 10 minutes using TMB, and then the color development was stopped using a stop solution. Thereafter, a microplate reader was used to measure the absorbance at a wavelength of 450 nm.

<Example 3> Monoclonal Phage Enzyme-Linked Immunosorbent Assay

To acquire monoclonal phages, SB media including carbenicillin (#C1389, Sigma) at a concentration of 50 ug/ml were dispensed in each well in a 96-well deep well plate (#90060, Bioneer), and colonies including the phage library were inoculated and cultured for 3 hours at 37° C. and 250 rpm. Afterwards, the M13K07 helper phage was treated at a concentration of $10^{10}$ phage/ml and cultured for another 2 hours under the same conditions. Thereafter, kanamycin (#K4000, Sigma) was treated at a concentration of 70 ug/ml, followed by culture overnight. When carrying out the phage enzyme-linked immunosorbent assay, some of the culture medium was treated after blocking, and the rest of the process was the same as the polyclonal phage enzyme-linked immunosorbent assay.

<Example 4> Purification Method Using High-Performance Liquid Chromatography The scFv sequence of a monoclone having a binding ability to GFRAL was transferred using sfiI restriction enzyme to an expression vector constructed based on a pFUSE vector (#pfuse hg1fc2, InvivoGen) and then transfected into Expi293F cells. Transfection was performed using ExpiFectamine 293 Transfection Kit (#A14524, Gibco). Expi293F cells were cultured in 500 ml flask with a density of approximately $2.5\times10^6$ cells/ml, and ExpiFectamine 293 Reagent and a vector expressing scFv were mixed and treated in the presence of Opti-MEM (#31985-070, Gibco) medium, followed by culture overnight at 37° C. and 125 rpm. The next day, ExpiFectamine 293 Transfection Enhancers 1 and 2 were treated and cultured for an additional 3 days to produce antibodies in the form of scfv-fc. The supernatant was then purified using an AKTA prime plus (GE healthcare) purifier and an IgG separation column (#17-0404-01, GE healthcare). The antibody was bound to the column with 20 mM sodium phosphate buffer (pH 7.4), and then an elution process was performed using 0.1 M glycine-hydrogen chloride buffer (pH 2.7). Concentration was carried out with Amicon Ultra-4-30K (#UFC803024, Millipore), followed by sterilization with a Spin-X filter (#8160, Corning). Endotoxin was removed using an endotoxin removal column (#88274, Thermo Fisher Scientific), and concentration was measured using a BCA kit (#23227, Thermo Fisher Scientific).

<Example 5> Antibody Enzyme-Linked Immunosorbent Assay 96-well half area plates were coated by reactions with recombinant human GFRAL or recombinant mouse GFRAL, or bovine serum albumin overnight at 4° C., followed by enzyme-linked immunosorbent assays using clonal scFv-Fc antibodies as the primary antibody and HRP-conjugated anti-human IgG antibody (#Ab97225, Abcam) as the secondary antibodies.

As a result of the experiment, as shown in FIG. 2 and FIG. 3, after 6 times of panning, the binding ability with GFRAL was identified by separating with monoclonal antibodies out of the finally selected antibodies, showing that the binding ability of M3 and M4 antibodies to mouse GFRAL was higher than that of the control clone A11. In addition, as shown in FIG. 4, it was found that the binding ability of M3 and M4 antibodies to human GFRAL was higher than that of the control clone A11.

<Example 6> Preparation of GFRAL/RET-Luciferase Reporter Cells by Transfection into HEK-293FT Cells HEK-293FT cells were inoculated in a 6-well plate with a density of approximately $1\times10^6$ cell/well, and Lipofectamine 2000 Reagent (#11668-027, Thermo Fisher Scientific), GFRAL-expressing vector (#OHu31183D, GenScript), and RET-expressing vector (#HG11997-CF, Sino Biological) were mixed and treated in a 1:1 ratio under Opti-MEM medium, followed by culture overnight at 37° C. The next day, the supernatant was removed and replaced with fresh medium supplemented with 10% fetal bovine serum. Afterwards, a vector that induces expression of luciferase during the ERK signaling process was injected and cultured overnight at 37° C., the supernatant was removed the next day, and a process of replacing with fresh medium supplemented with 10% fetal bovine serum was further proceeded.

<Example 7> Method of Converting from Monoclonal scFv Sequence to Human Antibody IgG Form The scFv sequence of the monoclone in the pFUSE vector was transferred using restriction enzymes to expression vectors constructed based on the pcDNA3.3-TOPO vector (#K830001, Invitrogen). A heavy chain variable regions was inserted in front of heavy chain constant regions 1-3 using ClaI restriction enzymes and NheI restriction enzymes, and a light chain variable region was inserted in front of light chain constant regions using ClaI restriction enzymes and BsiWI restriction enzymes and then transfected into Expi293F cells. Transfection was performed using the ExpiFectamine 293 Transfection Kit. Expi293F cells were cultured in 500 ml flasks with a density of about $2.5\times10^6$ cells/ml, and treatment was performed by mixing ExpiFectamine 293 Reagent and a vector expressing each chain of IgG in a 1:1 ratio in the presence of Opti-MEM medium, followed by culture overnight at 37° C. and 125 rpm. The next day, ExpiFectamine 293 Transfection Enhancers 1 and 2 were treated and cultured for another 3 days to produce intact IgG form of antibodies.

<Example 8> Analysis on Expression of Luciferase by Antibody

Transfected HEK-293FT cells were inoculated in 96-well plates with a density of about $7\times10^4$ cells/well, kept in a serodeficient state for 2 hours, and then treated and reacted with clonal antibodies for 2 hours. Human recombinant GDF15 was then treated for 5 minutes, and a degree of luminescence was measured using reagents (#E2610, Promega) including a substrate of luciferase enzyme.

As shown in FIG. 6, the experiment result showed that the luminous value increased when GDF15 was only treated and more decreased in a treatment concentration-dependent manner in the experimental group that was pretreated with M3 or M4 than in the control clone A11. As shown in FIG. 7 and FIG. 8, the obtained IC50 values were 1.959 μg/ml for control clone A11, 1.034 μg/ml for M3, and 1.354 μg/ml, revealing that M3 and M4 antibodies may inhibit GFRAL signaling with a smaller amount than the control clone A11. In addition, when switched to the human IgG form, it was more decreased in a treatment concentration-dependent manner in the experimental group that was pretreated with M3-IgG or M4-IgG than in the control clone A11-IgG, as shown in FIG. 9. As shown in FIG. 10 and FIG. 11, the obtained IC50 values were 29.08 μg/ml for the control clone A11-IgG, 4.889 μg/ml for M3-IgG, and 2.259 μg/ml for M4-IgG, revealing that M3-IgG and M4-IgG antibodies may inhibit GFRAL signaling with more than one-fifth smaller amount than the control clone A11-IgG.

<Example 9> Analysis on Mitigation of Cisplatin-Driven Cancer Cachexia Induction by Antibodies in an Allograft Mouse Tumor Model B16F10-Luc cells measured to be $1\times10^6$ cells were injected into mice aged 8 weeks, cisplatin was injected at a concentration of 10 mg/kg after the cancer grew to a certain size, and 10 mg/kg of clone A11 as a control and modified antibodies M3-IgG or M4-IgG having cancer cachexia mitigation efficacy were injected so as to determine whether the side effects induced by cisplatin were mitigated in the chemotherapy model. The drug was injected at intervals of twice a week.

As a result of experiment as shown in FIG. 12, it was found that the weight reduction effect induced by cisplatin in the chemotherapy situation was 13% more recovered for M3-IgG and 10% more for M4-IgG than in the group solely treated with cisplatin, and as shown in FIG. 13, it was found that appetite reduction effect was also 12% more mitigated for M3-IgG and 7% for M4-IgG. The specific changes in the fat and muscle weight were quantified as shown in FIG. 14 to FIG. 18. As a result, M3-IgG and M4-IgG increased fat mass and muscle mass compared to the group treated with cisplatin alone, and in particular, in the case of soleus muscle, it was found that M3-IgG significantly increased muscle mass by 20% and M4-IgG by 40% more than the group solely treated with cisplatin, thereby identifying the effect of mitigating reduction in the fat mass and muscle mass due to cancer cachexia induction.

As the specific parts of the present disclosure have been described in detail above, it is clear to those skilled in the art that these specific descriptions are merely preferred embodiment examples and do not limit the scope of the present disclosure. Accordingly, the substantial scope of the present disclosure will be defined by the appended claims and their equivalents.

The invention claimed is:

1. An anti-GFRAL antibody with improved affinity or an antigen-binding fragment thereof, comprising a heavy chain variable region which comprises a heavy chain CDR1 having an amino acid sequence represented by SEQ ID NO: 1, a heavy chain CDR2 having an amino acid sequence represented by SEQ ID NO: 2, and a heavy chain CDR3 having an amino acid sequence represented by SEQ ID NO: 3; and a light chain variable region which comprises a light chain CDR1 having an amino acid sequence represented by SEQ ID NO: 4, a light chain CDR2 having an amino acid sequence represented by SEQ ID NO: 5, and a light chain CDR3 having an amino acid sequence represented by SEQ ID NO: 6.

2. An anti-GFRAL antibody with improved affinity or an antigen-binding fragment thereof, comprising a heavy chain variable region which comprises a heavy chain CDR1 having an amino acid sequence represented by SEQ ID NO: 1, a heavy chain CDR2 having an amino acid sequence represented by SEQ ID NO: 7, and a heavy chain CDR3 having an amino acid sequence represented by SEQ ID NO: 8; and a light chain variable region which comprises a light chain CDR1 having an amino acid sequence represented by SEQ ID NO: 9, a light chain CDR2 having an amino acid sequence represented by SEQ ID NO: 10, and a light chain CDR3 having an amino acid sequence represented by SEQ ID NO: 6.

3. A method of preventing or treating anorexia or cachexia caused by an anticancer drug in a subject, comprising administering to the subject an effective amount of a pharmaceutical composition comprising the anti-GFRAL antibody with improved affinity according to claim 1 or an antigen-binding fragment thereof as an active ingredient.

4. The method of claim 3, wherein the anticancer drug is any one or more selected from the group consisting of cisplatin, oxaliplatin, carboplatin, procarbazine, mechlorethamine, cyclophosphamide, ifosfamide, melphalan, chlorambucil, busulfan, nitrosourea, dactinomycin, daunorubicin, doxorubicin, bleomycin, plicamycin, mitomycin, etoposide, tamoxifen, taxol, transplatinum, 5-fluorouracil, vincristine, vinblastine, and methotrexate.

5. A method of preventing or treating anorexia or cachexia caused by an anticancer drug in a subject, comprising administering to the subject an effective amount of a pharmaceutical composition comprising the anti-GFRAL antibody with improved affinity according to claim 2 or an antigen-binding fragment thereof as an active ingredient.

6. The method of claim 5, wherein the anticancer drug is any one or more selected from the group consisting of cisplatin, oxaliplatin, carboplatin, procarbazine, mechlorethamine, cyclophosphamide, ifosfamide, melphalan, chlorambucil, busulfan, nitrosourea, dactinomycin, daunorubicin, doxorubicin, bleomycin, plicamycin, mitomycin, etoposide, tamoxifen, taxol, transplatinum, 5-fluorouracil, vincristine, vinblastine, and methotrexate.

* * * * *

SEQUENCE LISTING

```
Sequence total quantity: 11
SEQ ID NO: 1            moltype = AA  length = 8
FEATURE                 Location/Qualifiers
source                  1..8
                        mol_type = protein
                        organism = synthetic construct
SEQUENCE: 1
```

```
GFTFSSYG                                                              8

SEQ ID NO: 2            moltype = AA  length = 8
FEATURE                 Location/Qualifiers
source                  1..8
                        mol_type = protein
                        organism = synthetic construct
SEQUENCE: 2
ISFDGSNK                                                              8

SEQ ID NO: 3            moltype = AA  length = 21
FEATURE                 Location/Qualifiers
source                  1..21
                        mol_type = protein
                        organism = synthetic construct
SEQUENCE: 3
CAKVTSGGDF LSGNYYYYMD V                                               21

SEQ ID NO: 4            moltype = AA  length = 6
FEATURE                 Location/Qualifiers
source                  1..6
                        mol_type = protein
                        organism = synthetic construct
SEQUENCE: 4
SLRDYY                                                                6

SEQ ID NO: 5            moltype =   length =
SEQUENCE: 5
000

SEQ ID NO: 6            moltype = AA  length = 11
FEATURE                 Location/Qualifiers
source                  1..11
                        mol_type = protein
                        organism = synthetic construct
SEQUENCE: 6
NSRGSSGNQW V                                                          11

SEQ ID NO: 7            moltype = AA  length = 8
FEATURE                 Location/Qualifiers
source                  1..8
                        mol_type = protein
                        organism = synthetic construct
SEQUENCE: 7
ISYDGSNK                                                              8

SEQ ID NO: 8            moltype = AA  length = 21
FEATURE                 Location/Qualifiers
source                  1..21
                        mol_type = protein
                        organism = synthetic construct
SEQUENCE: 8
CAKVTSGGDF WSGDYYWYMD V                                               21

SEQ ID NO: 9            moltype = AA  length = 6
FEATURE                 Location/Qualifiers
source                  1..6
                        mol_type = protein
                        organism = synthetic construct
SEQUENCE: 9
SLRDNK                                                                6

SEQ ID NO: 10           moltype =   length =
SEQUENCE: 10
000

SEQ ID NO: 11           moltype = AA  length = 21
FEATURE                 Location/Qualifiers
source                  1..21
                        mol_type = protein
                        organism = synthetic construct
SEQUENCE: 11
CAKVTSGGDF WSGNYYYYMD V                                               21
```